United States Patent
Olszak et al.

(10) Patent No.: US 7,864,379 B2
(45) Date of Patent: Jan. 4, 2011

(54) MULTI-SPECTRAL WHOLE-SLIDE SCANNER

(75) Inventors: Artur G. Olszak, Tucson, AZ (US); Chen Liang, Tucson, AZ (US)

(73) Assignee: DMetrix, Inc., Tucson, AZ (US)

( * ) Notice: Subject to any disclaimer, the term of this patent is extended or adjusted under 35 U.S.C. 154(b) by 1046 days.

(21) Appl. No.: 11/644,564

(22) Filed: Dec. 23, 2006

(65) Prior Publication Data

US 2007/0153370 A1 Jul. 5, 2007

Related U.S. Application Data

(63) Continuation-in-part of application No. 10/637,486, filed on Aug. 11, 2003, now Pat. No. 7,184,610, which is a continuation-in-part of application No. PCT/US02/08286, filed on Mar. 19, 2002.

(60) Provisional application No. 60/753,879, filed on Dec. 23, 2005, provisional application No. 60/276,498, filed on Mar. 19, 2001.

(51) Int. Cl.
*G02B 6/04* (2006.01)
*H04N 1/04* (2006.01)

(52) U.S. Cl. .................. 358/474; 358/484; 385/115

(58) Field of Classification Search ............ 358/474, 358/475, 496, 498, 484; 369/23, 44; 385/123, 385/31, 12, 13, 115, 116, 117, 118, 119, 385/120, 121, 147, 126, 127, 128; 359/738, 359/619, 321, 656; 250/216, 738, 227.11, 250/227.23, 234, 236, 306, 307, 227.24
See application file for complete search history.

(56) References Cited

U.S. PATENT DOCUMENTS

| | | | | |
|---|---|---|---|---|
| 5,052,238 A | * | 10/1991 | Sewell | 74/473.1 |
| 6,373,568 B1 | | 4/2002 | Miller et al. | |
| 6,396,053 B1 | * | 5/2002 | Yokoi | 250/234 |
| 6,690,466 B2 | | 2/2004 | Miller et al. | |
| 7,369,307 B2 | * | 5/2008 | Wolleschensky | 359/385 |
| 7,586,530 B2 | * | 9/2009 | Onozawa et al. | 348/294 |
| 7,697,382 B2 | * | 4/2010 | Mizutani et al. | 369/44.23 |
| 7,697,808 B2 | * | 4/2010 | D'Urso et al. | 385/115 |
| 2002/0036824 A1 | * | 3/2002 | Sasaki | 359/385 |
| 2005/0036197 A1 | * | 2/2005 | Awamura | 359/385 |
| 2009/0109527 A1 | * | 4/2009 | Sasaki et al. | 359/389 |
| 2009/0296207 A1 | * | 12/2009 | Goelles et al. | 359/385 |

* cited by examiner

*Primary Examiner*—Jerome Grant, II
(74) *Attorney, Agent, or Firm*—Antonio R. Durando

(57) ABSTRACT

An array microscope scans a slide in rapid sequence at different wavelengths to record multiple spectral images of the sample. Full spatial resolution of the image sensor is realized at each color because pixels are not shared between spectral bands. The object and detector are placed at conjugate distances selected to produce substantially equal magnification with minimum chromatic aberration at all wavelengths to ensure registration of all images. Spectral analysis is carried out by combining the images captured at each wavelength. The greater-than-RGB spectral resolution provided by the combination of images enables the isolation and display of the effects produced by the contemporaneous use of more than two stains on a tissue for improved pathological analysis.

17 Claims, 8 Drawing Sheets

MULTI-SPECTRAL WHOLE-SLIDE SCANNER

RELATED APPLICATIONS

This application is based on Provisional Application No. 60/753,879, filed Dec. 23, 2005, and is a continuation-in-part application of U.S. Ser. No. 10/637,486, filed Aug. 11, 2003, which is a continuation application of PCT/US02/08286, filed Mar. 19, 2002, and claims the benefit of priority of U.S. Provisional Application No. 60/276,498, filed Mar. 19, 2001, under 35 U.S.C. Sect. 119.

BACKGROUND OF THE INVENTION

1. Field of the Invention

This invention relates in general to the field of microscopy and, in particular, to a novel approach for providing multi-spectral illumination for pathologic analysis of tissue slides.

2. Description of the Prior Art

Changes in the cellular structure of tissue are used to detect pathologic changes, such as to assess the progress of precancerous conditions and to detect cancer. A tissue sample removed from a patient is typically sectioned and fixed to a slide for staining and microscopic examination by a pathologist. The morphology of the tissue (the visually perceptible structure and shape of features in the tissue) is analyzed to provide a qualitative assessment of its condition and to identify the presence of pathologic changes that may indicate progression towards a malignancy. For many decades, this visual procedure has been the diagnostic mainstay of pathology.

With the advent of computers and sophisticated digital imaging equipment, researchers have extended the realm of histopathology through the use of mechanized procedures for diagnostic and quantitative investigation. In such mechanized procedures, histopathologic sections and/or cytologic preparations are imaged with a microscope, and the images are digitized, stored, and analyzed for nuclear-placement patterns (histometry) or for the spatial and statistical distribution patterns of nuclear chromatin (karyometry). Karyometric assessment is always preceded by image segmentation, whereby each nucleus in an image is identified, outlined, isolated and stored as a separate image.

Each stain provides information on the localization of particular molecules in tissue or associated with different structural elements of the tissue section (e.g., nuclei). Therefore, a detailed knowledge of every stain's spatial distribution offers a distinct perspective about the biological material under review. Accordingly, localization of diverse stains in a single of tissue is a challenge of growing significance.

The conventional approach has been to employ at most two stains (e.g., hemotoxylin and eosin) in every tissue section because the human eye is often not capable of distinguishing pattern produced by additional stains. Increasing the number of stains can be problematic also for computerized analysis because of overlap between the stains' absorbance spectra. A conventional imaging system that captures a red, green, and blue ("RGB") image of the tissue section does not provide, for example, information that may be used unambiguously to separate the absorbance contributions of each stain at a detector pixel. Therefore, the use of more than two stains in the same tissue sample would not necessarily provide additional information with conventional microscopes even through mechanized analysis.

A desirable approach would be to stain the tissue sample with additional stains and collect more than three spectral channel images (colors) at every pixel, thereby providing sufficient spectral sampling to uniquely and unambiguously separate the absorbance contributions of each stain to each pixel of the detector. However, this approach has been difficult to implement with good results because of practical tradeoffs between source brightness, detector sensitivity and resolution, optics magnification, speed of acquisition, and computational requirements.

Systems for brightfield and fluorescence multispectral recording of specimens have been described (see U.S. Pat. No. 6,690,466 and U.S. Pat. No. 6,373,568 and are commercially available. Three different approaches are used to collect the multispectral information. For example, spectral filtering is used in the Nuance™ system sold by Cambridge Research and Instrumentation, Inc. ("Cri"), of Woburn, Mass.; scanning optical-path difference (OPD) in the interferometer SpectraView® sold by Applied Spectral Imaging, Inc., of Vista, Calif.; and diffraction grating in the LSM 510 META microscope manufactured by Carl Zeiss, Inc., of Germany. CRi's system has a spectral source constructed of multiple-color LEDs that can be individually controlled, thus allowing for an illumination source of adjustable spectrum. The light source can be used to either illuminate the sample with a sequence of "pure wavelengths" using one type of LED at a time or using a mixture of LEDs simultaneously.

All existing systems have in common the use of commercial microscope objectives and remain constrained by the field-of-view/numerical-aperture trade-off associated with these optical elements. These systems are primarily intended for collecting images of a single objective field of view rather than whole-slide scanning. Accordingly, these microscope optics enable two main image-acquisition approaches, by the so-called "step-and-repeat" and "push-broom" scanning modes. In the step-and-repeat approach, individual image fields (also known as "tiles") are recorded and the stage bearing the microscope slide is advanced to the next field, as illustrated in FIG. 1. For a typical 20× objective of approximately NA=0.75, this approach results in several thousand image fields for a 20×50 mm$^2$ slide, the exact number depending on how much field overlap is provided and on whether or not a complete record of the slide is made. The step-and-repeat approach is necessary when spectral data are acquired by a sequence of filters or by an interferometer; otherwise, the movement of the specimen will cause inconsistency in the collected spectral measurements.

Pushbroom scanning is based on the use of a linear detector array covering the diameter of field of view of the microscope objective. The approach results in a swath that could cover the entire length of a slide, to be repeated, after a step-over, typically 20-30 times to cover a 20 mm-wide slide. This approach is illustrated in FIG. 2.

A problem with both these image-acquisition approaches is that they require an overlap between the individual tiles or swath scans to ensure complete imaging coverage of the region of interest. Thus, stitching of image tiles or swaths and additional computation are required to determine the extent of redundant image data. Therefore, a more straightforward approach to generating multi-spectral images of tissue slides would represent a useful advance in the art. The present invention utilizes an array microscope to advantageously improve multi-spectral imaging of tissue slides.

SUMMARY OF THE INVENTION

In essence, the invention lies in the use of an array microscope that makes it possible to scan a whole sample slide in rapid sequence at different illumination wavelengths to record multiple spectral images of the same sample. As a result of this approach, full spatial resolution of the image sensor is realized at each color because pixels are not shared between spectral bands. The image quality and focus can be optimized separately at each color, instead of relying on conventional chromatic correction, which is not sufficiently perfect when implemented with commercially affordable optical elements, such as those made of plastic materials. Image-sensor response can be carefully calibrated separately for each color.

As a critical aspect of the invention, the various images collected at different wavelengths must be produced with the same magnification in order to ensure registration of all images. This is achieved by adjusting the position of the object and/or detector for each wavelength so that they are placed at the optimal conjugate distances from the objective array.

Image spectral analysis is carried out by combining the images captured at each wavelength to produce a vector of spectral responses for each detector pixel, thereby yielding spectral information that is not available when broadband illumination is used. On the basis of this information and the corresponding greater spectral resolution, the contemporaneous effects of a larger number of stains on a tissue sample may be isolated and displayed for improved pathological analysis. The summation of spectral images may be weighted in some fashion (such as by using a filter vector with positive and/or negative weights) to further improve the diagnostic significance of the spectral resolution produced by the invention.

Various other advantages will become clear from the description of the invention in the specification that follows and from the novel features particularly pointed out in the appended claims. Therefore, to the accomplishment of the objectives described above, this invention consists of features hereinafter illustrated in the drawings, fully described in the detailed description of the preferred embodiments, and particularly pointed out in the claims. However, such drawings and descriptions disclose only some of the various ways in which the invention may be practiced.

DETAILED DESCRIPTION OF THE INVENTION

Co-owned International Application PCT/US02/08286 and U.S. patent application Ser. No. 10/158,626, herein incorporated by reference, describe a new approach to microscopy. An array microscope is disclosed that comprises a plurality of optical imaging elements configured to image respective sections of an object and disposed with respect to an object plane so as to produce at respective image planes respective images of the respective sections of the object measurements. The object may be illuminated in a variety of ways, i.e., by transillumination, epi-illumination, or epi-fluorescence, as these terms are understood in the art.

Figure 1:
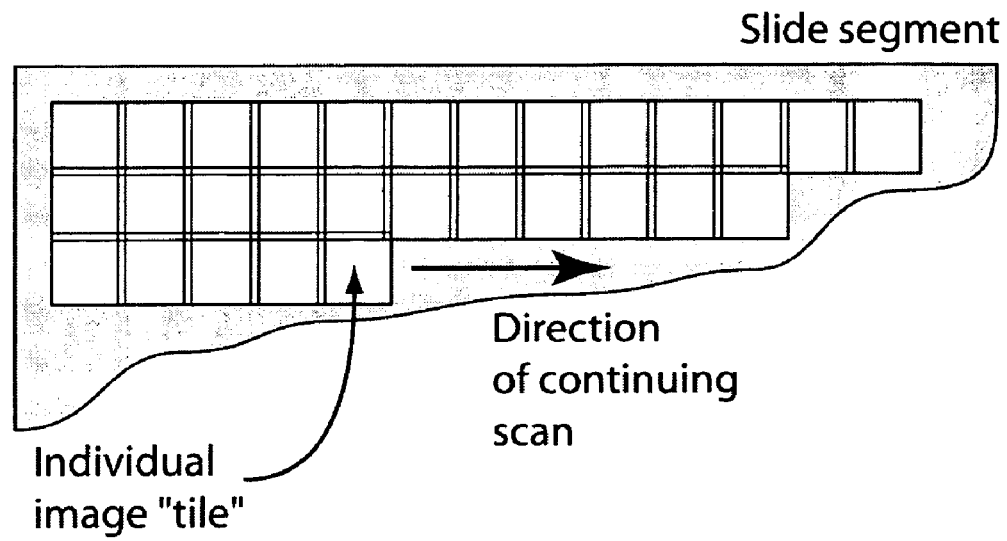
FIG. 1 is a schematic representation of the step-and-repeat approach used in conventional image scanning of sample slides using single-objective microscopes.
Figure 2:
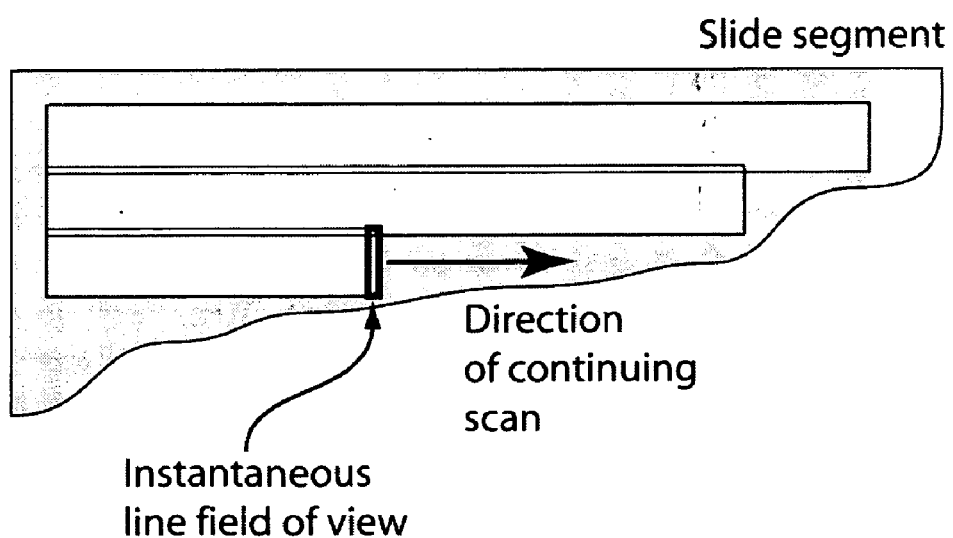
FIG. 2 is a schematic representation of the pushbroom approach used in conventional image scanning of sample slides using single-objective microscopes and linear detectors.
Figure 3:
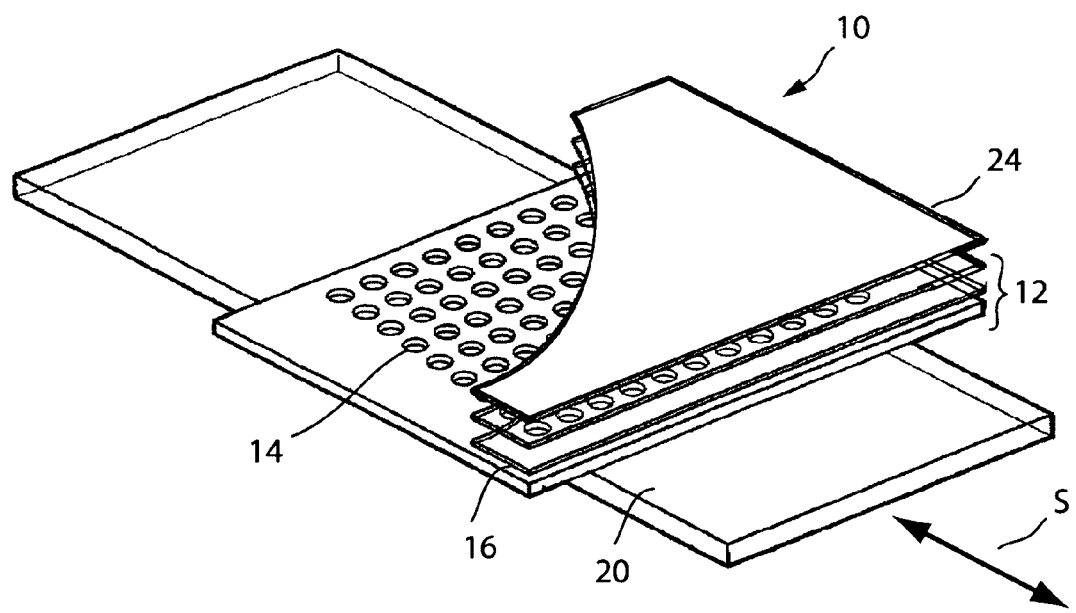
FIG. 3 is a simplified representation of the various components of the array microscope used to practice the invention.
Figure 4:
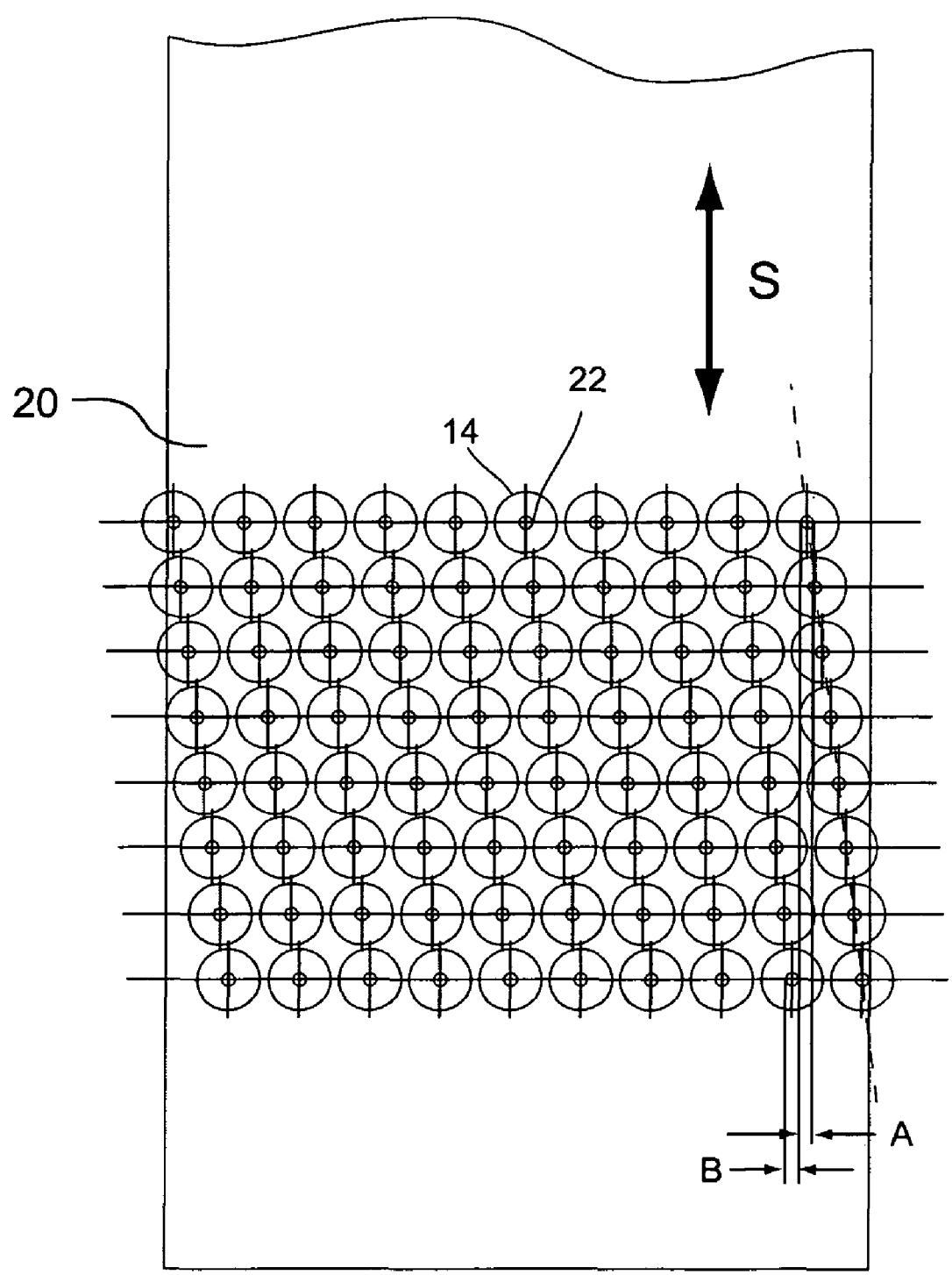
FIG. 4 illustrates in plan schematic view the staggered-row layout of the microscope array used to practice the invention.
Figure 5:
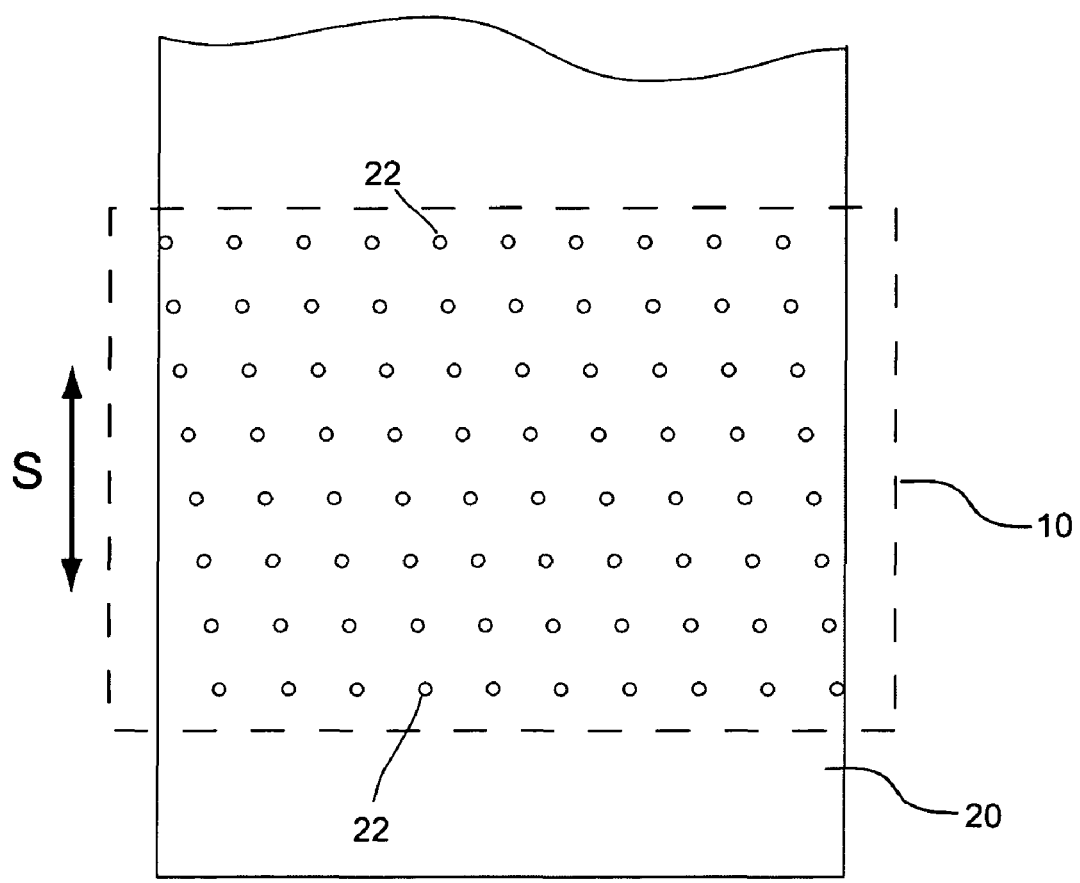
FIG. 5 illustrates in plan schematic view the staggered-row layout of the fields of view corresponding to the microscope array of FIG. 4.

As illustrated in FIG. 3, the array microscope 10 of Ser. No. 10/158,626 consists of a number of lens plates 12, each patterned with individual lenses 14 disposed in staggered rows which, coupled to other correspondingly staggered rows of lenses in parallel plates, form individual optical systems 16. As illustrated by arrow S, the array microscope 10 is translated along a linear direction of motion with respect to the object 20 (or vice versa). The rows of lenses in the array microscope are staggered with respect to the direction of scan, as shown in FIG. 4, and image frames are acquired during the scan across the object such that each of the optical systems 16 images a respective field of view 22, as illustrated in FIG. 5, and acquires images corresponding to a respective continuous strip of the object along the direction of scan (illustrated as A and B in FIG. 4).

Because of the staggered arrangement of the rows of lenses, the continuous strip covered by the linear scan of each optical system 16 is substantially free of overlap with continuous strips covered by other optical systems. Thus, at each acquisition frame each system 16 projects image data for a small section of the sample object 20 directly onto a pixel detector 24 and the sets of individual intensity data are then combined to form a composite image of the entire object by hardware and/or software manipulation. The details of implementation of array microscopes are disclosed in copending Ser. No. 10/158,626.

Figure 6:
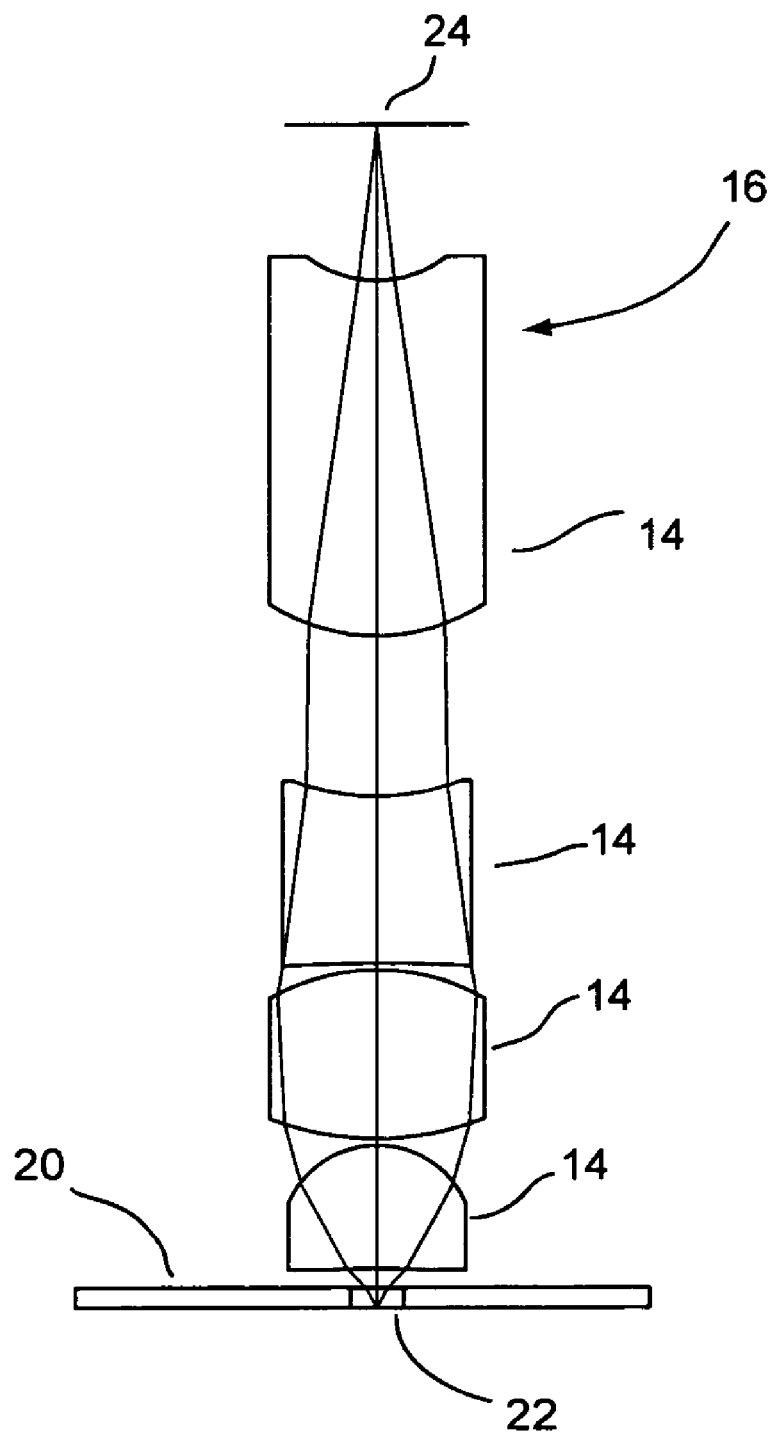
FIG. 6 illustrates the four-lens optical system of an individual miniature microscope with numerical aperture of 0.75 and the corresponding ray trace.

The use of array microscopes is based on the realization that small optical systems can provide good-quality, better-than RGB spectral resolution imaging with acceptable magnification. Accordingly, each individual optical system in the array is designed to perform such a function and a plurality of systems is packed together as closely as possible within the constraints of the physical size of each component. A typical individual microscope system used in an array microscope is shown in FIG. 6 and includes a set of lenses (generically referenced as lenses 14 in FIG. 3) specifically designed for a particular type of application. As illustrated, because of the magnification of the system and the need to avoid imaging overlaps on the detector 24, only a small field of view 22 can be captured at the detector plane within the area corresponding to each microscope system. In order to avoid overlaps, the detector 24 cannot be separated from the set of lenses 14 more than allowed by the system's magnification. Therefore, the lenses are necessarily packed very tightly in both lateral and axial directions.

According to the present invention, the array microscope of Ser. No. 10/158,626 is used to sequential, whole-slide images of the sample using different spectral sources, such as light diodes (LEDs). A collection of LED light sources, such as available from the Philips Lumileds Lighting Company of San Jose, Calif., is used to trans-illuminate in sequence the same glass slide. The glass slide is held in place, preferably using vacuum, during each scan in the sequence. Scanning can be performed in the same direction (only one direction of motion is necessary) or in two opposite directions. The latter approach results in a slightly faster operation of the scanner. With reference to the scanning direction of the imaging system of the invention, as described and claimed, the term "linear" is intended to cover a straight as well as a curvilinear path during which each objective of the microscope array acquires image data (light intensity) corresponding to a respective straight or curvilinear continuous strip of the object.

The process is preferably initiated by using the array microscope for a rapid, low-resolution scan of the glass slide with broadband light to assess generally the tissue and determine a region of interest. The resultant region, normally rectangular in shape, defines the length and width of the subsequent scans at each wavelength. Thus, the preferred configuration of the system is set up for scanning the same area of the slide at each wavelength of illumination.

Figure 7:
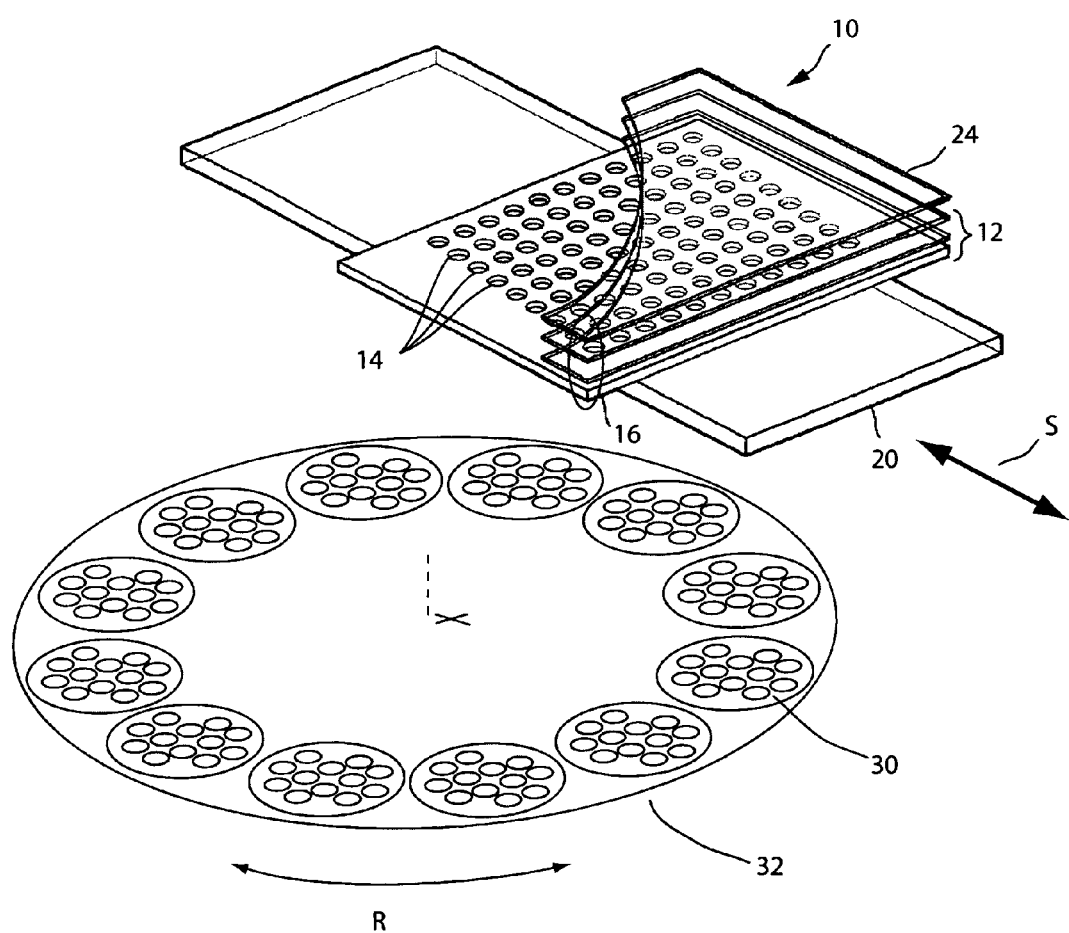
FIG. 7 illustrates a disk embodiment of the multi-spectral light source used to practice the invention in combination with the array microscope of FIG. 3.
Figure 8:
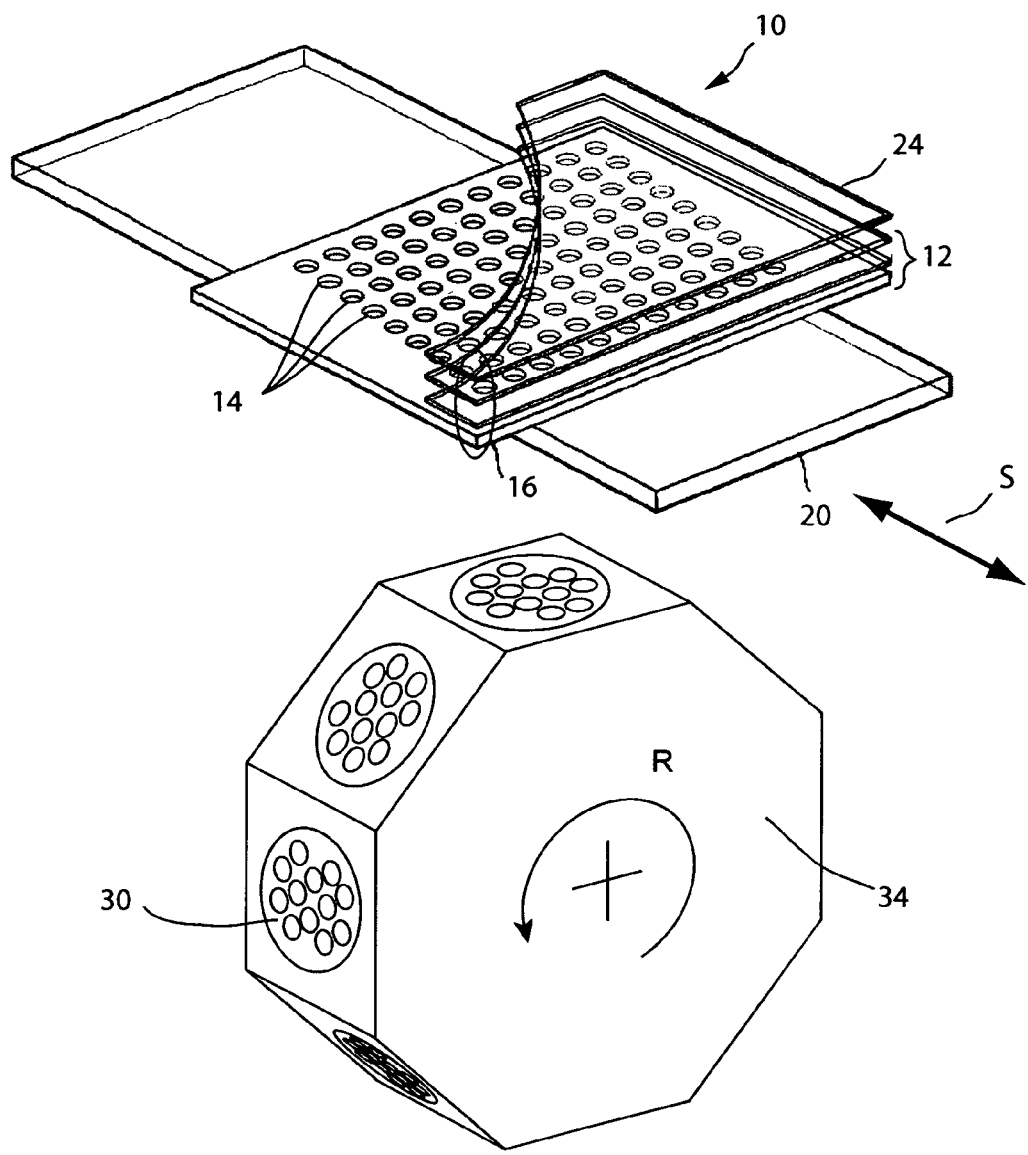
FIG. 8 is a drum embodiment of the light source of the invention combined with the array microscope of FIG. 3.

As illustrated in FIGS. 7 and 8, the preferred multi-spectral illumination system for the array microscope consists of a set of LED light sources 30, wherein each source preferably includes 7 to 12 LEDs of the same wavelength binned according to light-emission uniformity and center wavelength. This permits variable illuminating power levels to be used for different applications. The number of different wavelengths used to scan a sample is judiciously selected based on the number of stains applied to the sample. Up to 12 separate light sources 30 may be mounted on platter or disk 32 with multiple light sites, as shown in FIG. 7, or on a multi-sided drum 34, as shown in FIG. 8, rotatingly coupled to the microscope. Before each sequential scan of the same glass slide, the platter 32 is rotated through an appropriate angle to position the next LED light site under the condenser lens (not shown). Alternatively, the drum 34 is similarly rotated to place the desired LED light site into position under the condenser lens.

In multi-spectral imaging for computational analysis of information obtained from tissue slides stained with more than two colors, it is critical to have identical transverse magnification for all sampled wavelengths, so that the separate color images may be combined for meaningful analysis. The important point is to be able to measure the contribution of each wavelength to the measurements acquired at each pixel of the detector, thereby producing a color vector for each pixel that subsequently can be used to analyze the slide with respect to each stain used in the pathological process. Due to the unavoidable chromatic aberration associated with optical elements, the system of the invention needs to be corrected to guarantee a substantially constant transverse magnification at each wavelength used in the sequential scan.

In the microscope of the invention, which utilizes an array of custom-made objectives in the configuration of FIG. 6, a dynamic conjugate shift is used to produce constant magnification at different wavelengths over the visible spectrum while maintaining image quality. The object and image distances from the microscope array are adjusted each time images are taken at a different wavelength in order to maintain magnification and optimize image quality. This is done by means of a calibration procedure that involves varying the center wavelength with, for example, 15-nm steps (from 455 nm to 635 nm) while only using object and image distances as variables to achieve the desired magnification and image quality. The transverse magnification for each center wavelength is computed at multiple field positions from on-axis to full field. A typical result is shown in Table 1 below, where the value of transverse magnification is shown in its absolute value.

TABLE 1

Magnification for Different Field Positions and Center Wavelengths

| Field Position | Center Wavelength | | | | | | |
|---|---|---|---|---|---|---|---|
| | 455 | 470 | 485 | 500 | 515 | 530 | 545 |
| 0.08 | 7.005 | 7.0049 | 7.0051 | 7.0047 | 7.005 | 7.0045 | 7.0041 |
| 0.17 | 7.0055 | 7.0054 | 7.0055 | 7.0051 | 7.0054 | 7.0049 | 7.0045 |
| 0.25 | 7.0061 | 7.006 | 7.0061 | 7.0057 | 7.0061 | 7.0055 | 7.0051 |
| 0.33 | 7.0069 | 7.0068 | 7.0069 | 7.0065 | 7.0069 | 7.0063 | 7.0059 |
| 0.42 | 7.0077 | 7.0076 | 7.0077 | 7.0073 | 7.0077 | 7.0071 | 7.0067 |
| 0.50 | 7.0084 | 7.0083 | 7.0084 | 7.008 | 7.0083 | 7.0078 | 7.0074 |
| 0.58 | 7.0087 | 7.0086 | 7.0088 | 7.0083 | 7.0087 | 7.0082 | 7.0077 |
| 0.67 | 7.0085 | 7.0084 | 7.0086 | 7.0082 | 7.0086 | 7.008 | 7.0076 |
| 0.75 | 7.0074 | 7.0074 | 7.0076 | 7.0072 | 7.0076 | 7.0071 | 7.0067 |
| 0.83 | 7.0052 | 7.0052 | 7.0054 | 7.0051 | 7.0055 | 7.005 | 7.0047 |
| 0.92 | 7.0014 | 7.0015 | 7.0018 | 7.0015 | 7.002 | 7.0016 | 7.0013 |
| 1.00 | 6.9958 | 6.9959 | 6.9963 | 6.9961 | 6.9966 | 6.9963 | 6.996 |

| Field Position | Center Wavelength | | | | | |
|---|---|---|---|---|---|---|
| | 560 | 575 | 590 | 605 | 620 | 635 |
| 0.08 | 7.0041 | 7.0042 | 7.0048 | 7.0046 | 7.0039 | 7.004 |
| 0.17 | 7.0045 | 7.0046 | 7.0052 | 7.005 | 7.0043 | 7.0044 |
| 0.25 | 7.0052 | 7.0053 | 7.0059 | 7.0056 | 7.005 | 7.0051 |
| 0.33 | 7.0059 | 7.006 | 7.0066 | 7.0064 | 7.0057 | 7.0058 |
| 0.42 | 7.0067 | 7.0068 | 7.0074 | 7.0072 | 7.0065 | 7.0066 |
| 0.50 | 7.0074 | 7.0075 | 7.0081 | 7.0079 | 7.0072 | 7.0073 |
| 0.58 | 7.0078 | 7.0079 | 7.0085 | 7.0083 | 7.0076 | 7.0077 |
| 0.67 | 7.0077 | 7.0078 | 7.0084 | 7.0082 | 7.0075 | 7.0076 |
| 0.75 | 7.0068 | 7.0069 | 7.0075 | 7.0073 | 7.0067 | 7.0068 |
| 0.83 | 7.0048 | 7.005 | 7.0056 | 7.0054 | 7.0048 | 7.0049 |
| 0.92 | 7.0014 | 7.0016 | 7.0023 | 7.0021 | 7.0015 | 7.0017 |
| 1.00 | 6.9962 | 6.9965 | 6.9972 | 6.9971 | 6.9965 | 6.9967 |

As one skilled in the art would readily understand, the small amount of variation in transverse magnification produces a small difference in principal ray height on the image surface for different wavelengths at different field positions. A plot of this difference is shown in FIG. 9, which illustrates that a maximum difference of about 0.00017 mm occurs at full field (0.12 mm in radius for this particular microscope design), which is acceptable for image quality.

Figure 9:
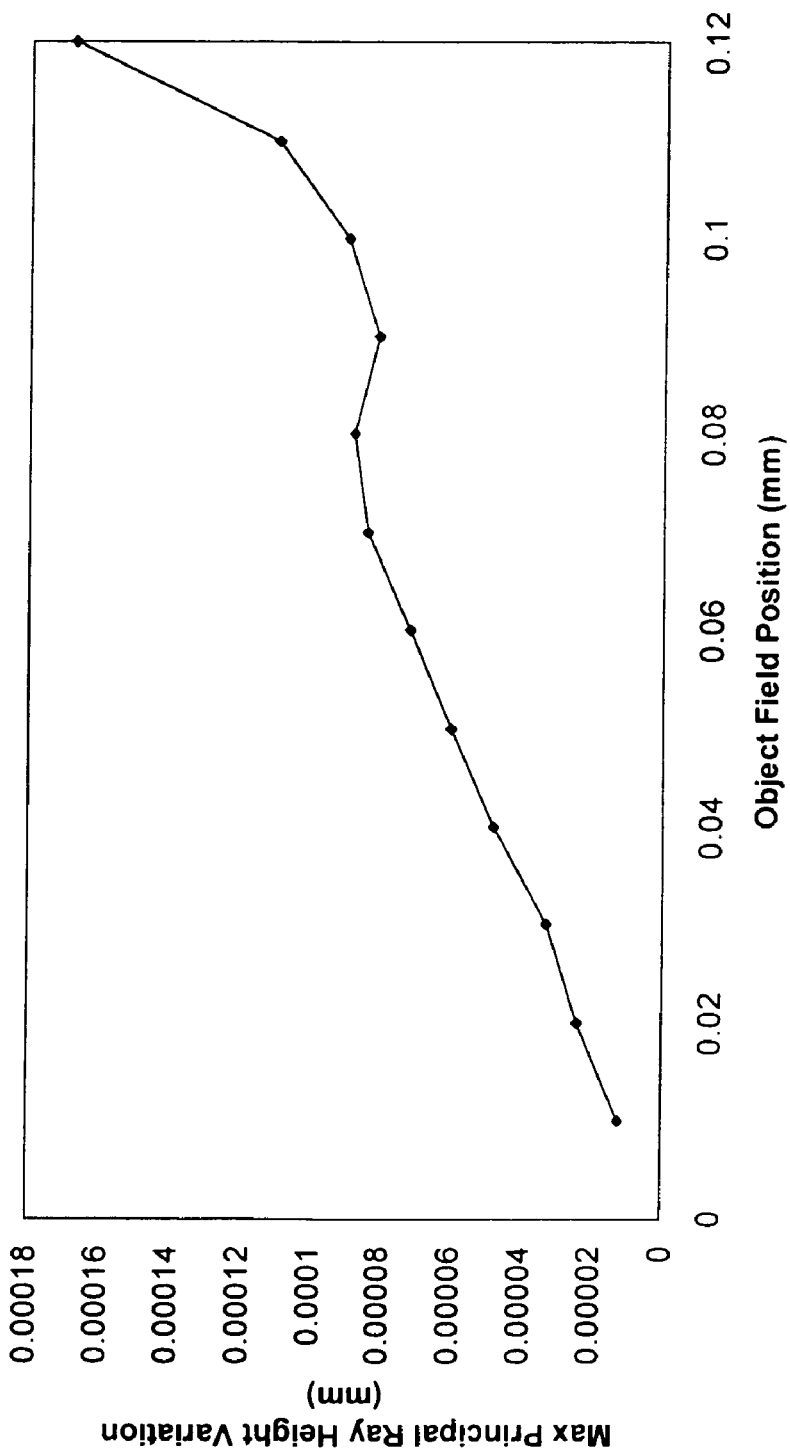
FIG. 9 is a plot illustrating spectral distortion as evidenced by the principal ray height variation as a function of wavelength for different field positions at the image surface of one objective in the array.

In order to achieve the substantially constant magnification reflected in FIG. 9, this exemplary objective would need to operate at specific object and image conjugate positions for each center wavelength. Given the objective's characteristics reflected in Table 1 and FIG. 9, these conjugate values may be calculated conventionally using the reported data and fixing the magnification criteria. Table 2 below shows the conjugate values corresponding to each center wavelength. The minimum value for Strehl Ratio (SR) across the field is also given in the table as a measure of acceptable for each center wavelength.

TABLE 2

Conjugate Values and Strehl Ratio (SR) as a Function of Wavelength.

| Center Wavelength | Min. SR | Obj Dis | Ima Dis |
|---|---|---|---|
| 455 | 0.934 | 0.374 | 1.629 |
| 470 | 0.947 | 0.377 | 1.642 |

TABLE 2-continued

Conjugate Values and Strehl Ratio
(SR) as a Function of Wavelength.

| Center Wavelength | Min. SR | Obj Dis | Ima Dis |
|---|---|---|---|
| 485 | 0.953 | 0.380 | 1.651 |
| 500 | 0.956 | 0.383 | 1.659 |
| 515 | 0.958 | 0.386 | 1.669 |
| 530 | 0.957 | 0.388 | 1.675 |
| 545 | 0.955 | 0.390 | 1.682 |
| 560 | 0.953 | 0.392 | 1.691 |
| 575 | 0.950 | 0.394 | 1.697 |
| 590 | 0.948 | 0.396 | 1.702 |
| 605 | 0.945 | 0.398 | 1.707 |
| 620 | 0.942 | 0.399 | 1.711 |
| 635 | 0.940 | 0.401 | 1.716 |

The approach illustrated above has several advantages. Very significantly for the purposes of pathology analysis, full spatial resolution of the image sensor is realized at each color because pixels are not shared between spectral bands. Furthermore, image quality and focus can be optimized at each separately, instead of relying on the imperfect chromatic correction provided even by an apochromatic microscope objective. Image-sensor response can be carefully calibrated for each color separately and image spectral analysis can be performed by storing weighted whole-slide image at each wavelength. Then, all spectral images may be summed at every pixel to provide a spectral filter vector with positive and/or negative weights as deemed necessary achieve desirable results. For example, a separate set of gains and offsets can be used for each color channel in order to equalize the variations among image-sensor detector responses and illumination variations. The gains and offsets can be modified by the introduction of a multiplicative factor that weighs a particular spectral image. The summation of the weighted, gain-and-offset-corrected, images results in a projection of each pixel's spectrum onto a vector, such as a particular principal component.

It is noted that these techniques of image manipulation are old in the art of spectral analysis. The contribution of this invention lies in an approach and tool for producing registered spectral images of the sample object with grater spectral resolution than heretofore possible.

In operation, the array microscope is first focused on the tissue mounted on the glass slide. This is done by performing a complete scan using at least one of the available illumination wavelengths, such as green, for example. A conventional autofocus approach may be used, focusing the array at each scan position to acquire and record the best-focus position according to the topography of the tissue as viewed by the objective, the tissue being mounted on the glass slide under the transparent cover glass or thin plastic tape typically used for pathology microscopy. A procedure for producing such a best-focus map is described, for example, in copending Ser. No. 10/431,937, hereby incorporated by reference.

The array microscope next scans the glass slide using one illumination color at a time. During each scan, the optics roll and pitch angles and the height of the array of objectives relative to the slide are adjusted to maintain focus at all individual objectives in the array on the basis of the information acquired during the initial auto-focus scan. In addition, for each illumination wavelength, the optics' object and image distances are adjusted, according to the invention, in order to maintain as much as possible a constant magnification throughout the field of view. This is achieved by shifting the trajectory obtained from the initial autofocus operation outlined above by an additional amount up or down according to the conjugates associated with each illumination color shown in Table 2.

As a result of this multi-spectral scanning process, the array microscope produces a series of registered spectral images. The registration is achieved, as explained, by an optical design that minimizes spectral dependence of distortion and a mechanical design that holds the glass slide securely in place during scanning. Based on current performance, the digital slide scanner described herein is capable of capturing each illumination-color image in approximately 18-19 seconds, covering a sample area of 15 mm by 15 mm.

Thus, it has been shown that the microscope array of the invention can be used advantageously to provide an improved tool for fast and reliable mechanized analysis of pathology slides. The improved spectral resolution produced by the invention makes it possible to stain tissue samples at the same time with more than two colors (the practical limit of prior art approaches), thereby enabling a more precise segmentation and identification of items of interest in the samples. This level of better-than-RGB spectral resolution, which is not visible in color images, also enables mechanized analysis that would not be possible by visual inspection of a pathologist, thereby improving the diagnostic efficacy of histopathology.

While the invention has been shown and described herein in what is believed to be the most practical and preferred embodiments, it is recognized that departures can be made therefrom within the scope of the invention. Therefore, it is not to be limited to the disclosed details but is to be accorded the full scope of the claims, including any and all equivalents thereof.

The invention claimed is:

1. A multi-spectral scanning microscope for imaging an object, comprising:

a plurality of discrete microscope objectives arranged in rows in a microscope array, said objectives being configured to image respective sections of the object during a scan of the object;

a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

a detector optically coupled to the microscope array for capturing image data representative of respective images of said sections of the object imaged by said plurality of objectives;

a light source adapted to illuminate the object at multiple distinct wavelengths;

a mechanism for placing the object and the detector at respective distances from the microscope array so as to maintain a substantially constant magnification at each of said distinct wavelengths; and a system for combining said image data captured by the detector during a sequence of scans of the scanning mechanism carried out at said multiple distinct wavelengths;

wherein said light source includes a multi-sided drum with a corresponding plurality of sites, each site being capable of emitting one of said distinct wavelengths, and the light source further includes a mechanism for rotating the drum to selectively illuminate the object with any one of said distinct wavelengths.

2. The scanning microscope of claim 1, wherein said light source includes light emitting diodes operating at each of said distinct wavelengths.

3. The scanning microscope system of claim 1, wherein said light source includes light emitting diodes operating at each of said distinct wavelengths.

4. The scanning microscope of claim 1, wherein said mechanism is adapted for placing the object and the detector at distinct conjugate distances from the microscope array corresponding to said distinct wavelengths.

5. A multi-spectral scanning microscope for imaging an object, comprising:
   a plurality of discrete microscope objectives arranged in rows in a microscope array, said objectives being configured to image respective sections of the object during a scan of the object;
   a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;
   a detector optically coupled to the microscope array for capturing image data representative of respective images of said sections of the object imaged by said plurality of objectives;
   a light source adapted to illuminate the object at multiple distinct wavelengths;
   a mechanism for placing the object and the detector at respective distances from the microscope array so as to maintain a substantially constant magnification at each of said distinct wavelengths; and
   a system for combining said image data captured by the detector during a sequence of scans of the scanning mechanism carried out at said multiple distinct wavelengths;
   wherein said light source includes a platter with a plurality of sites, each site being capable of emitting one of said distinct wavelengths, and the light source further includes a mechanism for rotating the platter to selectively illuminate the object with any one of said distinct wavelengths.

6. The scanning microscope of claim 5, wherein said light source includes light emitting diodes operating at each of said distinct wavelengths.

7. A multi-spectral scanning microscope for imaging an object, comprising:
   a plurality of discrete microscope objectives arranged in rows in a microscope array, said objectives being configured to image respective sections of the object during a scan of the object;
   a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;
   a detector optically coupled to the microscope array for capturing image data representative of respective images of said sections of the object imaged by said plurality of objectives;
   a light source adapted to illuminate the object at multiple distinct wavelengths;
   a mechanism for placing the object and the detector at respective distances from the microscope array so as to maintain a substantially constant magnification at each of said distinct wavelengths; and
   a system for combining said image data captured by the detector during a sequence of scans of the scanning mechanism carried out at said multiple distinct wavelengths;
   wherein said system for combining the image data captured by the detector during a sequence of scans at multiple distinct wavelengths includes a vector of weighting factors associated with each pixel of the detector.

8. A multi-spectral scanning microscope for imaging an object, comprising:
   a plurality of discrete microscope objectives arranged in rows in a microscope array, said objectives being configured to image respective sections of the object during a scan of the object;
   a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;
   a detector optically coupled to the microscope array for capturing image data representative of respective images of said sections of the object imaged by said plurality of objectives;
   a light source adapted to illuminate the object at multiple distinct wavelengths;
   a mechanism for placing the object and the detector at respective distances from the microscope array so as to maintain a substantially constant magnification at each of said distinct wavelengths; and
   a system for combining said image data captured by the detector during a sequence of scans of the scanning mechanism carried out at said multiple distinct wavelengths;
   wherein said light source includes a platter with a plurality of sites, each site being capable of emitting one of said distinct wavelengths, and the light source further includes a mechanism for rotating the platter to selectively illuminate the object with any one of said distinct wavelengths; said light source includes light emitting diodes operating at each of said distinct wavelengths; said mechanism is adapted for placing the object and the detector at distinct conjugate distances from the microscope array corresponding to said distinct wavelengths; and said system for combining the image data captured by the detector during a sequence of scans at multiple distinct wavelengths includes a vector of weighting factors associated with each pixel of the detector.

9. A method for multi-spectral imaging of an object, comprising the steps of:
   providing a plurality of discrete microscope objectives arranged in rows in a microscope array, said objectives being configured to image respective sections of the object during a scan of the object;

providing a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

providing a pixel detector optically coupled to the microscope array for capturing image data representative of respective images of said sections of the object imaged by said plurality of objectives;

providing a light source adapted to illuminate the object at multiple distinct wavelengths;

providing a mechanism for placing the object and the detector at respective distances from the microscope array so as to maintain a substantially constant magnification at each of said distinct wavelengths;

scanning the object sequentially, using each of said distinct wavelengths, after having placed the object and the detector at said respective distances; and combining image data captured by the detector during said sequential scanning step to provide a composite spectral image of the object;

wherein the sequential scanning step is preceded by a scan using an auto-focus mechanism to produce a best-focus map for said microscope objectives at each acquisition position along said scan of the object, and further by the step of applying the best-focus map to the microscope array during the sequential scanning step.

10. The method of claim 9, wherein said respective distances from the microscope array to maintain a substantially constant magnification at each of said distinct wavelengths mechanism are conjugate distances from the microscope array corresponding to the distinct wavelengths.

11. The method of claim 9, wherein said light source includes light emitting diodes operating at each of said distinct wavelengths.

12. A method for multi-spectral imaging of an object, comprising the steps of:

providing a plurality of discrete microscope objectives arranged in rows in a microscope array, said objectives being configured to image respective sections of the object during a scan of the object;

providing a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

providing a pixel detector optically coupled to the microscope array for capturing image data representative of respective images of said sections of the object imaged by said plurality of objectives;

providing a light source adapted to illuminate the object at multiple distinct wavelengths;

providing a mechanism for placing the object and the detector at respective distances from the microscope array so as to maintain a substantially constant magnification at each of said distinct wavelengths;

scanning the object sequentially, using each of said distinct wavelengths, after having placed the object and the detector at said respective distances; and combining image data captured by the detector during said sequential scanning step to provide a composite spectral image of the object;

wherein said light source includes a multi-sided drum with a corresponding plurality of sites, each site capable of emitting one of said distinct wavelengths, and the light source further includes a mechanism for rotating the drum to selectively illuminate the object with said distinct wavelengths during said sequential scanning step of the object.

13. The method of claim 12, wherein said light source includes light emitting diodes operating at each of said distinct wavelengths.

14. A method for multi-spectral imaging of an object, comprising the steps of:

providing a plurality of discrete microscope objectives arranged in rows in a microscope array, said objectives being configured to image respective sections of the object during a scan of the object;

providing a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

providing a pixel detector optically coupled to the microscope array for capturing image data representative of respective images of said sections of the object imaged by said plurality of objectives;

providing a light source adapted to illuminate the object at multiple distinct wavelengths;

providing a mechanism for placing the object and the detector at respective distances from the microscope array so as to maintain a substantially constant magnification at each of said distinct wavelengths;

scanning the object sequentially, using each of said distinct wavelengths, after having placed the object and the detector at said respective distances; and combining image data captured by the detector during said sequential scanning step to provide a composite spectral image of the object;

wherein said light source includes a platter with a plurality of sites, each site capable of emitting one of said distinct wavelengths, and the light source further includes a mechanism for rotating the platter to selectively illuminate the object with said distinct wavelengths during said sequential scanning step of the object.

15. The method of claim 14, wherein said light source includes light emitting diodes operating at each of said distinct wavelengths.

16. A method for multi-spectral imaging of an object, comprising the steps of:

providing a plurality of discrete microscope objectives arranged in rows in a microscope array, said objectives being configured to image respective sections of the object during a scan of the object;

providing a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

providing a pixel detector optically coupled to the microscope array for capturing image data representative of respective images of said sections of the object imaged by said plurality of objectives;

providing a light source adapted to illuminate the object at multiple distinct wavelengths;

providing a mechanism for placing the object and the detector at respective distances from the microscope array so as to maintain a substantially constant magnification at each of said distinct wavelengths;

scanning the object sequentially, using each of said distinct wavelengths, after having placed the object and the detector at said respective distances; and combining image data captured by the detector during said sequential scanning step to provide a composite spectral image of the object;

wherein said step of combining the image data captured by the detector during a sequence of scans at multiple distinct wavelengths includes applying a vector of weighting factors.

17. A method for multi-spectral imaging of an object, comprising the steps of:

providing a plurality of discrete microscope objectives arranged in rows in a microscope array, said objectives being configured to image respective sections of the object during a scan of the object;

providing a scanning mechanism for producing said scan as a result of a relative movement between the microscope array and the object, wherein the scan is implemented along a linear direction of scan across the object and said rows of objectives are staggered with respect to the direction of scan, such that during the scan each of the objectives acquires image data corresponding to a respective continuous strip of the object along the direction of scan;

providing a pixel detector optically coupled to the microscope array for capturing image data representative of respective images of said sections of the object imaged by said plurality of objectives;

providing a light source adapted to illuminate the object at multiple distinct wavelengths;

providing a mechanism for placing the object and the detector at respective distances from the microscope array so as to maintain a substantially constant magnification at each of said distinct wavelengths;

scanning the object sequentially, using each of said distinct wavelengths, after having placed the object and the detector at said respective distances;

combining image data captured by the detector during said sequential scanning step to provide a composite spectral image of the object; and preceding the sequential scanning step with a scan using an auto-focus mechanism to produce a best-focus map for said microscope objectives at each acquisition position along said scan of the object, and applying the best-focus map to the microscope array during the sequential scanning step;

wherein said respective distances from the microscope array to maintain a substantially constant magnification at each of said distinct wavelengths mechanism are conjugate distances from the microscope array corresponding to the distinct wavelengths; said light source includes a platter with a plurality of sites, each site capable of emitting one of said distinct wavelengths, and the light source further includes a mechanism for rotating the platter to selectively illuminate the object with said distinct wavelengths during said sequential scanning step of the object; said light source includes light emitting diodes operating at each of said distinct wavelengths; and said step of combining the image data captured by the detector during a sequence of scans at multiple distinct wavelengths includes applying a vector of weighting factors.

* * * * *